United States Patent [19]

Graefe et al.

[11] Patent Number: 5,427,992

[45] Date of Patent: Jun. 27, 1995

[54] PROCESS FOR PREPARING SOLUTIONS OF OLIGOMERIC METHYLALUMINOXANES

[75] Inventors: Jürgen Graefe, Selm-Cappenberg; Stefan Gurtzgen, Wuppertal; Karl H. Müller, Werne; Jürgen Schneider; Rolf Schrader, both of Unna, all of Germany

[73] Assignee: WITCO GmbH, Bergkamen, Germany

[21] Appl. No.: 941,660

[22] Filed: Sep. 8, 1992

Related U.S. Application Data

[63] Continuation of Ser. No. 784,369, Oct. 29, 1991, abandoned, which is a continuation of Ser. No. 601,199, Oct. 22, 1990, abandoned.

[30] Foreign Application Priority Data

Feb. 14, 1990 [DE] Germany .................. 40 04 477.77

[51] Int. Cl.$^6$ ............................................. B01J 31/00
[52] U.S. Cl. .................................... 502/111; 502/117; 502/152; 502/179
[58] Field of Search .................. 502/152, 111, 117; 556/179

[56] References Cited

U.S. PATENT DOCUMENTS

| | | |
|---|---|---|
| 3,242,099 | 3/1966 | Manyik et al. ................ 502/117 |
| 3,996,012 | 12/1976 | Zucker . |
| 4,146,520 | 3/1979 | Bierwirth et al. . |
| 4,404,344 | 9/1983 | Sinn et al. . |
| 4,542,199 | 9/1985 | Kaminsky et al. . |
| 4,544,762 | 10/1985 | Kaminsky et al. . |
| 4,665,046 | 5/1987 | Campbell, Jr. . |
| 4,665,047 | 5/1987 | Slaugh et al. . |
| 4,668,838 | 5/1987 | Briggs ........................... 502/117 X |
| 4,730,071 | 3/1988 | Schoenthal et al. ............... 556/179 |
| 4,730,072 | 3/1988 | Schoenthal et al. ............... 556/179 |
| 4,769,510 | 9/1988 | Kaminsky et al. . |
| 4,772,736 | 9/1988 | Edwards et al. . |
| 4,912,075 | 3/1990 | Chang ........................... 502/111 X |

FOREIGN PATENT DOCUMENTS

| | | |
|---|---|---|
| 1247297 | 12/1988 | Canada . |
| 0098372 | 1/1984 | European Pat. Off. . |
| 0128046 | 12/1984 | European Pat. Off. . |
| 0208561 | 1/1987 | European Pat. Off. . |
| 0232595 | 8/1987 | European Pat. Off. . |
| 0237294 | 9/1987 | European Pat. Off. . |
| 0241560 | 10/1987 | European Pat. Off. . |
| 0257695 | 3/1988 | European Pat. Off. . |
| 0258924 | 3/1988 | European Pat. Off. . |
| 0315234 | 5/1989 | European Pat. Off. . |
| 3240382 | 3/1984 | Germany . |
| WO8703887 | 7/1987 | WIPO . |
| WO8902453 | 3/1989 | WIPO . |

*Primary Examiner*—Asok Pal
*Attorney, Agent, or Firm*—Scully, Scott, Murphy & Presser

[57] ABSTRACT

The invention relates to a process for preparing solutions of oligomeric methylaluminoxanes, which contain trimethylaluminum in the free and/or complexed form, in hydrocarbons by partial hydrolysis of trimethylaluminum with water and to carrying out this process in a rotor/stator reaction machine.

The product obtained is suitable for preparing highly active polymerization catalysts.

27 Claims, 2 Drawing Sheets

PROCESS FOR PREPARING SOLUTIONS OF OLIGOMERIC METHYLALUMINOXANES

This is a continuation of application Ser. No. 784,369, filed on Oct. 29,1991, now abandoned, which is a continuation of Ser. No. 601,199, filed on Oct. 22, 1990, now abandoned.

BACKGROUND

The invention relates to the preparation of solutions of oligomeric methylaluminoxanes which, if desired, may contain higher alkyl groups and which contain trimethylaluminum in a free and/or complexed form; the solvents used here are aliphatic, cycloaliphatic or aromatic hydrocarbons.

Longer-chain oligomeric and/or polymeric alkylaluminoxanes of the simplified structures

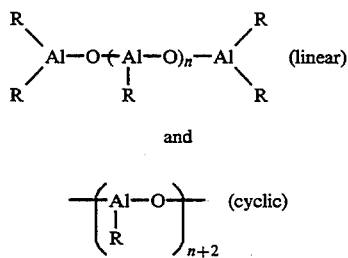

are known compounds which arc used as catalyst components in the preparation of highly active polyolefin catalysts, oligomeric methylaluminoxanes (MAO) with $R=CH_3$ being sometimes mentioned as being preferred (DE-A-3,007,725, EP-B-O,069,951, DE-A-3,240,382, EP-A-O,170,059, DE-A-3,443,087, EP-B-O,128,046, U.S. Pat. No. 4,665,046, EP-A-O,232,595, U.S. Pat. Nos. 4,668,838, 4,665,047, EP-A-O,241,560, WO87/03,887 and EP-A-O,237,294).

The reaction of aluminum trialkyls with water in inert hydrocarbons is here mentioned as a known preparation process for alkylaluminoxanes. Mainly, however, other methods are mentioned as preferred for the preparation oligomeric methylaluminoxanes (MAO) from trimethylaluminum (TMA), since it is known from the literature that, according to the preparation procedure described in more detail in, for example, U.S. Pat. No. 3,242,099, MAO can be prepared only with difficulty and in a very poor yield by slow addition of water to trimethylaluminum (TMA) (EP-A-O,108, 339); in addition, products are then obtained which, together with the transition metal component, do not give highly active catalyst systems (EP-B-O,069,951).

In this connection, it is stated explicitly in J. Polymer Science, 23, No. 8 (page 2120): "Simple synthetic routes to the methylaluminoxane $[O-Al(CH_3)-]_n$ are not available owing to the extremely high reactivity of the parent trimethylalane. This notwithstanding, the synthesis through direct reaction between $Al(CH_3)_3$ and $H_2O$ in a 1:1 molar ratio in toluene solution has been reported. We found this method not very reliable. The degree of oligomerization of the resulting aluminoxane was scarcely reproducible and the reaction rather uncontrollable."

These shortcomings were to be eliminated by reacting trimethylaluminum (TMA) with salts containing water of crystallization, such as aluminum sulfate hydrate (EP-A-O,108,339), or generally hydrates of salts of a type which are not reduced under the reaction conditions (EP-A-O, 208,561), or, in another procedure, by reacting TMA with inorganic substances which contain water bound by absorption or adsorption, such as finely dispersed silica (WO-A-89/02, 453), alumina (WO-A-89/02,453), hydrated alumina (EP-A-O,315,234) or molecular sieves (doctorate thesis I. Herwig, Hamburg University, 1979).

The last-mentioned preparation methods involve, of course, additional expense on equipment and operating costs; they have the considerable disadvantage that the solids used must as a rule be comminuted and screened (especially salts containing water of crystallization), so that they can readily be metered, and in addition their water content must be precisely adjusted and controlled for a specific and reproducible reaction. Moreover, long reaction times and, at least at the start of the reaction, frequently low temperatures are required (EP-A-O,315,234, WO-A-89/02,453), which results not only in correspondingly lower space/time yields, but also in higher expense on equipment and/or energy.

There was therefore a demand for a simple process for preparing oligomeric MAO, which gives a good yield of product which is soluble in inert hydrocarbons and with specific transition metal compounds, gives highly active catalyst systems for the polymerization of olefins.

SUMMARY OF THE INVENTION

Such a process is provided by the invention. By the process according to the invention, solutions of oligomeric methylaluminoxanes (MAO) which, if desired, may contain higher alkyl groups and which contain trimethylaluminum (TMA) in a free and/or complexed form, are prepared by reacting a solution of TMA and, if desired, further aluminum alkyls in inert aliphatic, cycloaliphatic or aromatic hydrocarbons, preferably toluene, with water in an $H_2O$/TMA molar ratio of from 0.65 to 0.75 and subsequently separating off the insoluble by-products formed in the reaction. The resulting clear solutions of oligomeric MAO can be employed directly without further purification steps for the preparation of polymerization catalysts.

DETAILED DESCRIPTION OF THE INVENTION

Figure 1:
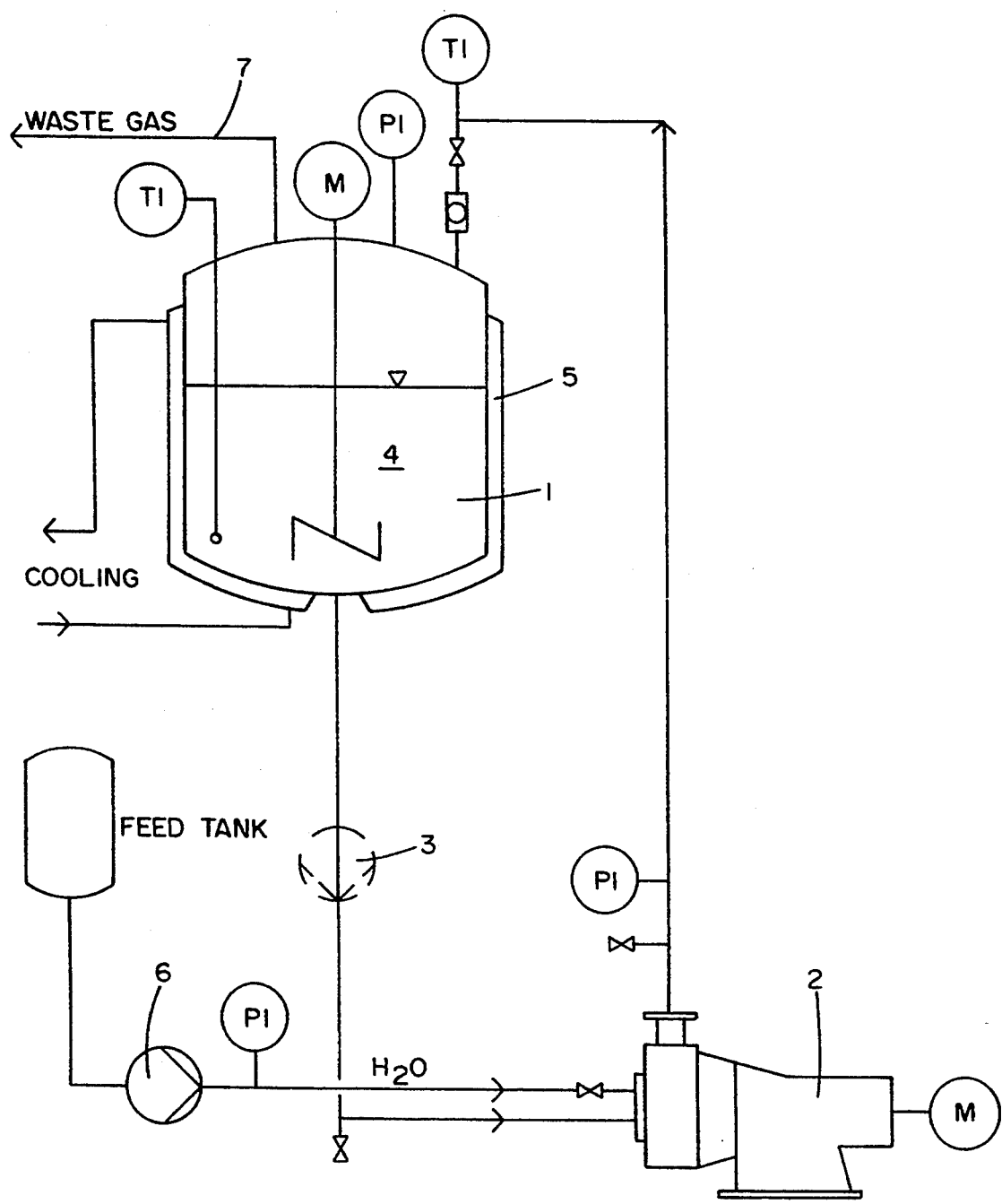
FIG. 1 is a schematic of the apparatus, including the various parts, such as the stirrer vessel and the rotor/stator reaction machine, and the various connections thereto, which could be used in the preparation of solutions of oligomeric methyl aluminoxanes according to the present invention.

As used herein, the term alkyl groups refers to an and alkyl group containing 1-10 carbon atoms. It includes methyl, ethyl, propyl, isopropyl, butyl, isobutyl, sec-butyl, t-butyl, pentyl, hexyl, isopentyl, heptyl, octyl, nonyl and decyl. Methyl is the preferred alkyl group.

The starting materials are here employed in such quantities that the concentration of the MAO in the solvent used is in the range from 1 to 20% by weight, preferably 1 to 10% by weight. The concentrations can then be increased by removing the solvent by distillation under mild conditions, preferably to 10 to 50% by weight of MAO. Even solid methylaluminoxane (MAO) can be obtained in this way by complete removal of the solvent. Unconverted TMA, some of which also passes over when the solvent is removed by condensation, can advantageously be re-used for the preparation of MAO.

The solvents which are used in this reaction are inert hydrocarbon solvents containing just carbon and hydrogen atoms. It is preferred that aromatic hydrocarbons, i.e., benzene and especially alkylbenzenes which are mono-, di-, or trialkylsubstituted, with each alkyl group containing 1-3 carbon atoms, be used. The preferred alkylbenzenes are toluene and xylene. Other hydrocarbon solvents that may be used are the saturated aliphatic hydrocarbons containing 5-8 carbon atoms, e.g., pentane, hexane, heptane, octane and the like. Heptane is preferred. Cycloaliphatic hydrocarbons, containing 5-7 carbon atoms, e.g., cyclopentane and cyclohexane can also be used.

The reaction is preferably carried out by adding water slowly to a solution of TMA in one of the abovementioned hydrocarbons, the reaction temperature being maintained in a range from $-50°$ C. to $100°$ C. As a rule, however, it is sufficient to operate at a temperature from 0 to $50°$ C.

In order to avoid uncontrolled reactions, in view of the relatively high exothermic heat of the reaction of TMA with water, the addition of the water to the solution of TMA should take place slowly and, at the same time, adequate heat removal should be ensured. Insoluble by-products which arise are separated from the solution by conventional measures, such as filtration, centrifuging or decanting.

Because of the reactivity of TMA and MAO to atmospheric oxygen, the preparation of MAO must be carried out under an inert gas atmosphere.

The reaction product obtained is a solution of an oligomeric methylaluminoxane (MAO) which contains unconverted TMA in a free and/or complexed form. Such a solution is particularly highly suitable as a catalyst component for the preparation of highly active polyolefin catalysts. The MAO can also, as described in Example 1, be isolated in a solid form. The solid is an oligomer having a mean molecular weight of from about 800 to 3000 g/mol.

Methylaluminoxanes which additionally contain higher alkyl groups in the range from 5-20 mol % relative to methyl, preferably 10-15 mol %, can also be prepared by the process according to the invention. As used herein the term higher alkyl group refers to an alkyl group containing more than one carbon atom. Higher alkyl groups that may be present on the methyl aluminoxanes include ethyl, butyl, isobutyl, hexyl and octyl. The incorporation of the higher alkyl groups results in a higher solubility in hydrocarbons, which is of advantage especially in the case of aliphatic hydrocarbons, for example, heptane (Example 7), since pure MAO is only sparingly soluble in such solvents (Example 6).

In contrast to the opinion hitherto prevailing in expert circles, according to which an $H_2O$/TMA molar ratio of about 1 must be maintained for preparing an active MAO (U.S. Pat. No. 3,242,099, EP-A-0,241,560, EP-A-0,208,561) and according to which catalytically active MAO is not obtainable by adding water to TMA—see, for example, U.S. Pat. No. 3,242,099 or J. Polymer Science 23, No. 8, page 2120)—it was surprising that, according to the simple and inexpensive process according to the invention, solutions of MAO, which in combination with specific transition metal complexes are distinguished by a high catalytic activity in the polymerization of olefins, are obtainable by reacting TMA and water at an $H_2O$/TMA molar ratio of from 0.65 to 0.75. In this range, a very active MAO is obtained which has adequately high mean molecular weight and a good stability in alkylbenzenes, for example, toluene. In the procedure described in Examples 1 to 3, MAO is thus obtained in yields of 46-48%, relative to isolated solid. The content of insoluble by-products is relatively low and can readily be separated off.

It has been found that the yield of soluble MAO falls drastically above an $H_2O$/TMA molar ratio of 0.75, especially at a molar ratio close to 1. Moreover, the reaction proceeds with extensive formation of foam, and a very pronounced precipitation of a white solid appears (Comparative Example 1).

If, however, the $H_2O$/TMA molar ratio is decreased below the range from 0.65 to 0.75, according to the invention, the yield of MAO rapidly drops, so that the process becomes uneconomical (Comparison Examples 2 and 3).

Since it is of advantage to ensure thorough mixing of the reactants, various technical measures have been proposed for the preparation of MAO, such as, for example, ultrasonics (EP-A-0,257,695) or stirrers having extremely high speeds of rotation ("high shear-inducing impeller"-EP-A-0,258,924).

However, a further improvement of the process according to the invention was not to be found when these techniques were used. Only MAO yields of 42% or 44% of theory respectively, relative to isolated solid, were obtained (Comparison Examples 4 and 5).

In addition, when the above-mentioned mixing techniques according to EP-A-0,257,965 and EP-A-0,258,924 are used in accordance with the instructions and starting material ratios given therein, MAO solutions of very low concentration (1-2% by weight) are obtained.

Particularly good reaction results are in fact obtained, surprisingly, and even outside the preferred range of the $H_2O$/TMA molar ratio from 0.65 to 0.75, if the water required for the reaction is added to the feed solution of TMA in a hydrocarbon in the region of the turbulence field of a rotor/stator reaction machine.

The structure and function of such a rotor/stator reaction machine is described, for example, in DE-A-2,363, 888.

Figure 2:
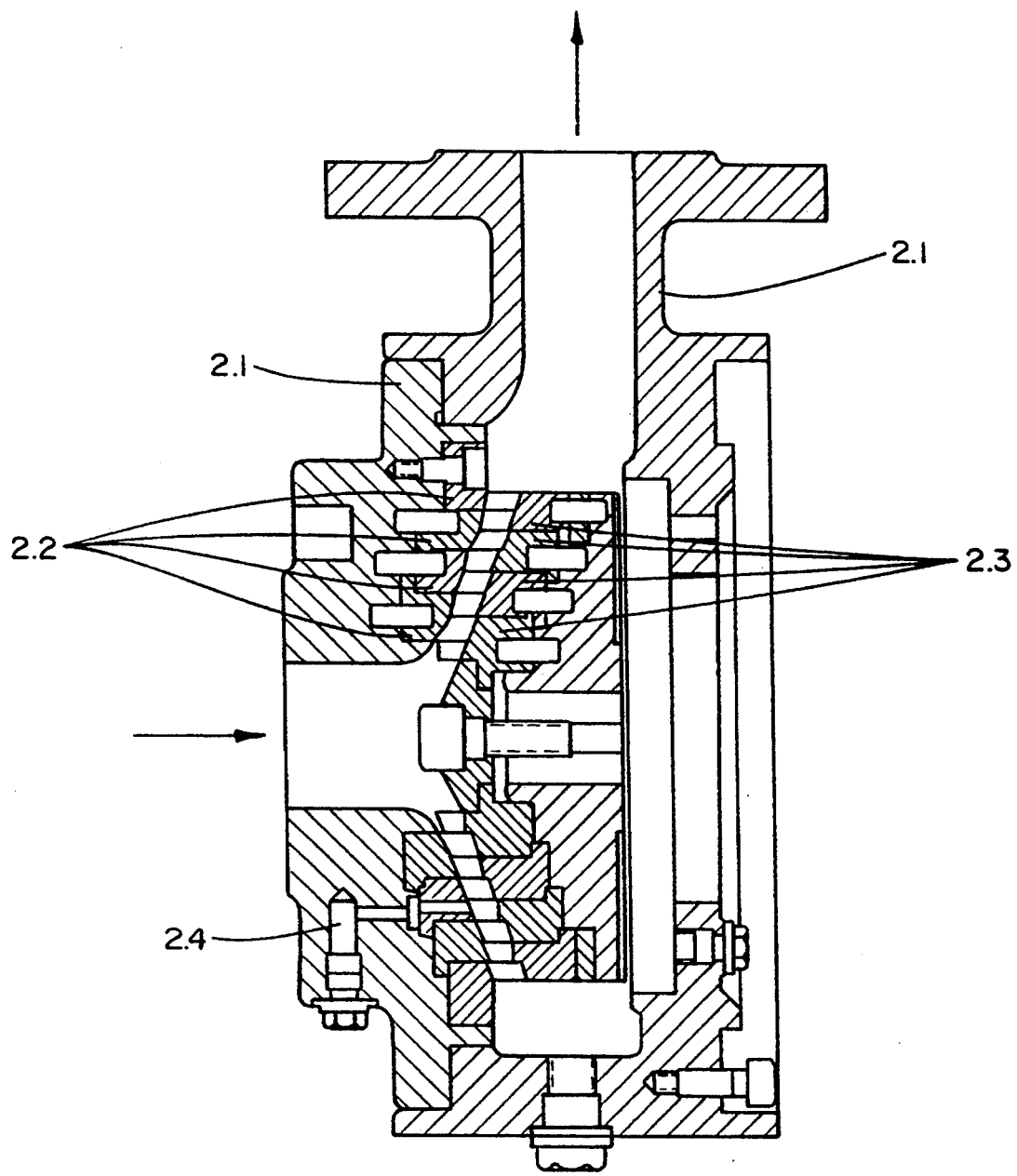
FIG. 2 is a diagrammatic view of one part of the assembly of FIG. 1, viz., the rotor/stator reaction machine and particularly shows a rotating rotor and a stationary stator defining therebetween a reaction zone through which the trimethylaluminum is alternately subjected to compression and expansion.

As can be seen from FIG. 2, one stator tool set (2.2) and one rotor tool set (2.3) are located in a housing (2.1). Both tool sets consist of concentrically arranged, annular individual tools which are provided with slots or bores milled in radially. They are constructionally designed in such a way that they run at a small mutual gap clearance.

The stator tool set is mounted in a fixed position in the machine, while the rotor tool set is driven at a high speed of rotation. The rotor tool set thus rotates in the annular gaps between the individual stator tool rings in such a way that one tool ring runs in the interspace between two other tool rings.

When passing through the machine, the reaction components are alternately accelerated centrifugally in the rotor tools and given a high peripheral speed, in order to be braked again the next stationary stator tool and deflected in the radial direction. High shear forces are thus built up. Owing to the speed of rotation and the tool configuration, this step takes place at such a frequency that particularly good turbulence of the product is obtained and a reactant which is introduced into the system through a metering bore (4) at a suitable point in the housing is homogeneously incorporated within fractions of a second into the reaction mixture flowing through the machine and can be caused to react spontaneously. It is immaterial here whether the machine is set up inside a conventional stirrer vessel or externally.

The process according to the invention is explained more in detail below by reference to FIG. 1.

Advantageously, the TMA solution is first introduced into a conventional stirrer vessel (1) which operates in conjunction with the rotor/stator reaction machine (2), the content of the stirrer vessel being fed to the rotor/stator reaction machine by gravity flow or by means of a pump (3) and being returned to the stirrer vessel after it has left the reaction machine.

The reaction of TMA with water takes place in the reaction machine (2) which is set up externally and into which the water is metered by means of a metering pump (6) in the region of the turbulence field. The homogeneous incorporation of the water, described above, is here assisted and reinforced by the evolution of methane gas, which takes place during the reaction with TMA. The stirrer vessel contents (4) flowing through the reaction machine then flow back again into the stirrer vessel (1), where the heat of reaction generated and the heat additionally introduced by the drive power is removed by appropriate heat exchange surfaces (5) and any amounts of waste gas which may have formed are separated from the liquid and removed via the waste gas exit line (7).

As can be seen from Examples 4 and 5, this process using a rotor/stator reaction machine represents a surprisingly simple variant for the economical preparation of MAO from TMA and water on an industrial scale. It is particularly distinguished by high yields and high space-time yields of MAO. Only subordinate quantities of solid by-products are obtained. The technically very simple construction with, at the same time, a readily controllable reaction procedure allows the preparation of MAO in reproducible quality with very short reaction times. An increase in the yield of soluble MAO by more than 20% can thus be achieved. Moreover, the reaction can conveniently be carried out at room temperature, which entails a significant saving in the cooling energy.

EXAMPLE 1

1047 g of a solution of 92.3 g (1.28 mol) of trimethylaluminum (TMA) in 954.7 g of toluene were put into a 2 liter three necked flask which was provided with a stirrer, a cooler, a 10 ml three ring syringe and a nitrogen buffer system. The solution was cooled to 2° C. With stirring and external cooling, 15.8 g (0.88 mol) of distilled water were then added dropwise through the three-ring syringe within about 2 hours at an internal temperatures of from 2° to 6° C. The methane formed in the reaction was passed into an extraction hood. The $H_2O$/TMA molar ratio was 0.7.

At the start of the reaction, a formation of mist in the gas space and cloudiness in the reaction solution could be observed. With progressive addition of the water, formation of a white solid insoluble in the reaction mixture started.

After completion of the addition of water, the reaction mixture was heated to 50° C. and boiled under reflux under reduced pressure (about 100 mbar), in order to remove dissolved methane. Insoluble by-products were then separated off by filtration under nitrogen. After drying in vacuo, the quantity of insoluble by-product was 25 g or 27% (relative to TMA employed).

As the filtrate, 925.5 g of a clear and colorless solution were obtained which contained MAO in a soluble form and unconverted TMA. The Al content of the solution was 2.5% by weight. Accordingly, this solution contained 23.1 g (0.86 g atom) of Al. The yield of Al in solution, relative to Al in the TMA employed, was thus 67%. The proportion of Al which was detectable by titration with isoquinoline was 1.0% by weight, corresponding to a quantity of 9.24 g (0.34 g atom) of Al. 104 g of the solution thus obtained were subjected to a vacuum distillation under mild conditions. In this way, 4.8 g of MAO were isolated as a white solid, corresponding to a yield of 46%, relative to Al in the TMA employed. The Al content of the isolated solid was 39.6% by weight. 8.3% by weight of Al were detected by titration with isoquinoline. 533 ml (S.T.P.)/g of methane were formed on hydrolysis of the solid. The mean molecular weight was determined to be 1500 g/mol (cryoscopy in benzene).

EXAMPLE 2

Analogously to Example 1, water and TMA were reacted in a molar ratio of 0.65.

As the filtrate, 912 g of a clear and colorless solution were obtained which contained soluble MAO and unconverted TMA. The Al content of the solution was 2.7% by weight.

The filtrate was then concentrated in a distillation apparatus by distilling off 501 g of toluene under reduced pressure (about 100 mbar). 8 g of TMA or 8.7% of the TMA employed were present in toluene distilled off.

As the concentrate, 400 g of a clear and colorless solution were obtained which contained soluble MAO and residual TMA. The Al content of the concentrate was 5.1% by weight. Accordingly, the concentrate contained 20.4 g (0.76 g atom) of Al, corresponding to a yield of 59%, relative to Al in the TMA employed. The proportion of Al which was detectable by titration with isoquinoline was 1.5% by weight, corresponding to a quantity of 6.0 g (0.22 g atom) of Al.

60 g of the 400 g of concentrate were subjected to a vacuum distillation under mild conditions. In this way, 6.7 g of MAO were isolated as a white solid. Accordingly, the yield of oligometric MAO which can be isolated is 48%, relative to Al in the TMA employed.

The Al content of the isolated solid was 42.4% by weight. 7% by weight of Al were detected by titration with isoquinoline. 515 ml (S.T.P.)/g of methane were formed in the hydrolysis of the solid. The mean molecular weight was determined to be 1200 g/mol (cryoscopy in benzene).

EXAMPLE 3

Analogously to Example 1, water and TMA were reacted in a molar ratio of 0.75.

The yield of isolated, oligomeric MAO was 48%, relative to Al in the TMA employed. The mean molecular weight was about 2500 g/mol (cryoscopy in benzene).

EXAMPLE 4

A solution of 7.6 kg (105.5 mol) of TMA in 40.0 kg of toluene was caused to react with 1.211 kg (67.3 mol) of distilled water in a 100 l stainless steel reactor coupled to a rotor/stator machine (Supraton type, made by Krupp). The water was metered in by means of a piston metering pump (Lewa type, 3 mm capillary diameter, metering time: 3.5 hours, 30 minutes time for completing the reaction). After filtration, 4.15 kg of MAO solution with a content of 5.5% by weight of Al were obtained (82% of theory relative to Al). The content of solid oligomeric MAO was determined to be 11.1% by weight (68% of theory relative to Al) by vacuum distillation of an aliquot part of the solution under mild conditions.

EXAMPLE 5

The procedure was analogous to that in Example 4, with the only difference that the $H_2O$/TMA molar ratio was 0.5. After working-up, a solution resulted which contained 5.4% of Al (87% of theory relative to Al). Removal of the solvent from 155 g of filtrate gave 12.5 g of MAO solid (51% of theory relative to Al).

EXAMPLE 6

Analogously to Example 1, 150.0 g (2,083 mol) of trimethylaluminum in 850 g of heptane were introduced first, and 23.8 g (1.322 mol) of water were metered in at 0° C. ($H_2O$:TMA molar ratio=0.64). After the end of metering, the resulting suspension was stirred for about a further 2 hours at room temperature and then filtered. 958 g of filtrate were obtained whose Al content was determined to be 4.04% by weight (yield: 65% of theory relative to Al). Removal of the solvent by evaporation in vacuo gave 25.4 g of solid (20% of theory relative to Al).

EXAMPLE 7

Analogously to Example 1, 46.0 g (0.634 mol) of trimethylaluminum and 18.5 g (0.091 mol) of triisobutylaluminum in 196 g of heptane were introduced first, and 8.48 g (0.471 mol) of water were metered in such that the temperature did not exceed 20° C. Working up analogously to Example 4 gave 213 g of filtrate having an Al content of 5.8% by weight (63% of theory relative to Al). 21.0 g of solid (36% of theory relative to Al) were obtained from 80 g of the filtrate by removal of the solvent in vacuo.

Comparative Example 1

A solution of 39.6 g (0.55 mol) of TMA in 409.4 g of toluene was put into a 1-liter three necked flask which was fitted out as in Example 1. Under conditions analogous to those in Example 1, 9.9 g (0.55 mol) of water were then added dropwise ($H_2O$/TMA molar ratio=1.0). In this case, very pronounced formation of foam started after the addition of about 8 g of water ($H_2O$/TMA molar ratio about 0.8) and this impeded complete thorough mixing of the total reaction mixture and made it necessary to slow down the addition of water. After working up, 28% of oligomeric MAO were isolated, relative to TMA employed. The proportion of by-product insoluble in toluene was 54%, relative to Al in the TMA employed.

Comparative Example 2

Analogously to Example 1, water and TMA were reacted in a molar ratio of 0.4.

The yield of oligomeric MAO which could be isolated was 29% relative to Al in the TMA employed.

Comparative Example 3

Analogously to Example 1, water and TMA were reacted in a molar ratio of 0.5.

The yield of oligomeric MAO which could be isolated was 26% relative to Al in the TMA employed.

Comparative Example 4

Analogously to Example 1, 39 g (0.54 mol) of TMA, dissolved in 156 g of toluene, were reacted with 6.3 g (0.35 mol) of distilled water, corresponding to an $H_2O$:TMA molar ratio of 0.65. An ultrasonic probe (20 kHz 150 W) was used in place of the KPG stirrer. 160 g of a colorless filtrate as clear as water were obtained, whose Al content was determined to be 5.22% by weight (58% of theory relative to Al in the TMA). 110 g of the filtrate were freed of solvent by evaporation in vacuo. This gave 11.0 g of solid (=42% of theory relative to Al in the TMA).

Comparative Example 5

Analogously to Example 1, 61 g (0.83 mol) of TMA, dissolved in 244 g of toluene, were reacted with 9.7 g (0.54 mol) of distilled water, corresponding to an $H_2O$:TMA molar ratio of 0.65. An ultraturrax stirrer was used in place of the KPG stirrer. After filtration, 258 g of a colorless filtrate as clear as water were obtained which had an Al content of 5.6% by weight (65% of theory relative to Al in the TMA). 177 g of the filtrate were freed of solvent by evaporation in vacuo. This gave 18.0 g of solid (=44% of theory relative to Al in the TMA).

What is claimed is:

1. A process for preparing oligomeric methylaluminoxanes in solution which comprises adding water to trimethylaluminum in an aliphatic, cycloaliphatic or aromatic hydrocarbon solvent under an inert gas atmosphere, such that the molar ratio of water to trimethylaluminum ranges from about 0.65 to about 0.75, reacting the water with said trimethylaluminum and removing the insoluble by-products therefrom.

2. The process according to claim 1 wherein the solvent is alkylbenzenes.

3. The process according to claim 1 wherein the reaction is carried out at temperatures of from about −50° C. to about 100° C.

4. The process according to claim 3 wherein the reaction is carried out at a temperature of from about 0° to about 50° C.

5. The process according to claim 1 wherein the resulting solution of methylaluminoxanes is concentrated by removing the solvent.

6. The process according to claim 5 wherein the concentration of the solution is adjusted to about 10% to 50% by weight of alkylaluminoxane.

7. A process according to claim 1 wherein the methylaluminoxanes are isolated in the solid form by removal of the solvent from the solution obtained.

8. A process for preparing a solution of oligomeric methylaluminoxanes comprising adding sufficient water to react with trimethylaluminum under an inert gas atmosphere in an aliphatic, cycloaliphatic or aromatic hydrocarbon solvent in a rotor/stator reaction machine to form said oligomeric methylaluminoxanes, said addition taking place in the region of said reaction machine subjected to a turbulence field.

9. A process for preparing a solution of oligomeric methylaluminoxane which comprises adding trimethylaluminum in solution in an aliphatic, cycloaliphatic or aromatic hydrocarbon solvent into a stirrer vessel which feeds said solution at a continuous and uniform rate through connecting means into a rotor/stator reaction machine and adding sufficient water to react with said trimethylaluminum solution in the reaction area of said rotor/stator reaction machine subjected to a turbulence field to form said oligomeric methylaluminoxanes.

10. The process according to claim 9 wherein the trimethylaluminum is fed into the rotor/stator reaction machine by means of gravity flow or by a pump.

11. The process according to claim 9 wherein water is added by means of a metering pump.

12. The process according to claim 1 wherein the methyl aluminoxanes are present from 1-20% by weight.

13. The process according to claim 1 wherein the water is added dropwise to the trimethylaluminum.

14. A process for preparing a solution of oligomeric methylaluminoxanes comprising adding water to react with trimethylaluminum under an inert gas atmosphere in an aliphatic, cycloaliphatic or aromatic hydrocarbon solvent in a rotor/stator reaction machine to form said oligomeric methylaluminoxanes, such that the molar ratio of water to trimethylaluminum ranging from about 0.65 to about 0.75, said addition taking place in the region of said reaction machine subjected to a turbulence field.

15. A process for preparing a solution of oligomeric methylaluminoxane which comprises adding trimethylaluminum in solution in an aliphatic, cycloaliphatic or aromatic hydrocarbon solvent into a stirrer vessel which feeds said solution at a continuous and uniform rate through connecting means into a rotor/stator reaction machine and adding sufficient water to react with said trimethylaluminum solution in the reaction area of said rotor/stator reaction machine subjected to a turbulence field to form said oligomeric methylaluminoxanes such that the molar ratio of water to trimethylaluminum ranges from about 0.65 to about 0.75.

16. The process according to claim 15 wherein the trimethylaluminum is fed into the rotor/stator reaction machine by means of gravity flow or by a pump.

17. The process according to claim 16 wherein water is added by means of a metering pump.

18. The process according to claim 15 wherein the solvent is alkyl benzene.

19. The process according to claim 15 wherein the reaction is carried out at 0° C. to about 50° C.

20. The process according to claim 15 wherein the reaction is carried out at about room temperature.

21. The process according to claim 15 wherein the resulting solution of oligomeric methylaluminoxanes is concentrated by removing the solvent.

22. The process according to claim 21 wherein the concentration of the solution is adjusted to about 10% to 50% by weight of the methylaluminoxanes.

23. The process according to claim 16 wherein the solvent is alkyl benzene.

24. The process according to claim 16 wherein the reaction is carried out at 0° C. to about 50° C.

25. The process according to claim 16 wherein the reaction is carried out at about room temperature.

26. The process according to claim 16 wherein the resulting solution of methylaluminoxanes are concentrated by removing the solvent.

27. The process according to claim 26 wherein the concentration of the solution is adjusted to about 10% to 50% by weight of the methylaluminoxanes.

* * * * *

UNITED STATES PATENT AND TRADEMARK OFFICE
CERTIFICATE OF CORRECTION

PATENT NO. : 5,427,992
DATED : June 27, 1995
INVENTOR(S) : Jurgen Graefe, et al.

It is certified that error appears in the above-indentified patent and that said Letters Patent is hereby corrected as shown below:

On the Title Page, item [30]: "40 04 477.77" should read --40 04 477.7--

Column 1, line 30: "arc" should read --are--

Signed and Sealed this

Second Day of July, 1996

Attest:

BRUCE LEHMAN

Attesting Officer

Commissioner of Patents and Trademarks